US012778381B2

(12) United States Patent
Nielsen et al.

(10) Patent No.: US 12,778,381 B2
(45) Date of Patent: Nov. 3, 2026

(54) MEDICAL VISUALISATION DEVICE WITH WIRELESS TRANSMISSION

(71) Applicant: AMBU A/S, Ballerup (DK)

(72) Inventors: Brian Nielsen, Næstved (DK); Kasper Rieland Jakobsen, Roskilde (DK); Chun-Chieh Chen, Rødovre (DK)

(73) Assignee: AMBU A/S, Ballerup (DK)

(*) Notice: Subject to any disclaimer, the term of this patent is extended or adjusted under 35 U.S.C. 154(b) by 261 days.

(21) Appl. No.: 18/276,868

(22) PCT Filed: Mar. 1, 2022

(86) PCT No.: PCT/EP2022/055133
§ 371 (c)(1),
(2) Date: Aug. 10, 2023

(87) PCT Pub. No.: WO2022/184702
PCT Pub. Date: Sep. 9, 2022

(65) Prior Publication Data

US 2024/0130605 A1 Apr. 25, 2024
US 2024/0225417 A9 Jul. 11, 2024

(30) Foreign Application Priority Data

Mar. 5, 2021 (DK) .......................... PA 2021 70098

(51) Int. Cl.
*A61B 1/00* (2006.01)
*A61B 1/05* (2006.01)
(Continued)

(52) U.S. Cl.
CPC ...... *A61B 1/00016* (2013.01); *A61B 1/00045* (2013.01); *A61B 1/00103* (2013.01);
(Continued)

(58) Field of Classification Search
CPC ...... A61B 1/00016; A61B 1/05; A61B 1/0676
See application file for complete search history.

(56) References Cited

U.S. PATENT DOCUMENTS 4,646,721 A 3/1987 Arakawa
5,450,293 A 9/1995 Hoffman
(Continued)

FOREIGN PATENT DOCUMENTS

CN 103188987 A 7/2013
EP 1827258 B1 10/2011
(Continued)

OTHER PUBLICATIONS

Corrected International Search Report received for PCT/EP2022/055134, mailed Jul. 26, 2022, 5 pages., Jul. 26, 2022.
(Continued)

*Primary Examiner* — Rochelle D Turchen
(74) *Attorney, Agent, or Firm* — Faegre Drinker Biddle & Reath LLP

(57) ABSTRACT

A medical visualisation system including a medical visualisation device having: an image sensor configured to generate image data, a light emitter, a device processing unit configured to receive the image data from the image sensor and encode the image data to provide encoded image data based on the image data, and a device wireless transceiver configured to communicate with a monitor wireless transceiver of a monitor device, the device wireless transceiver being configured to receive the encoded image data from the device processing unit and transmit the encoded image data using a downstream data channel from the device wireless transceiver to the monitor wireless transceiver and to receive settings data using an upstream data channel from the monitor wireless transceiver to the device wireless transceiver.

18 Claims, 6 Drawing Sheets

(51) Int. Cl.
*A61B 1/06* (2006.01)
*A61B 1/267* (2006.01)
*A61B 1/005* (2006.01)

(52) U.S. Cl.
CPC .............. *A61B 1/05* (2013.01); *A61B 1/0676* (2013.01); *A61B 1/267* (2013.01); *A61B 1/0004* (2022.02); *A61B 1/005* (2013.01)

(56) References Cited

U.S. PATENT DOCUMENTS

| | | | |
|---|---|---|---|
| 5,940,126 A | 8/1999 | Kimura | |
| 6,106,457 A | 8/2000 | Perkins et al. | |
| 6,796,939 B1 | 9/2004 | Hirata et al. | |
| 7,520,853 B2 | 4/2009 | Amling et al. | |
| 7,753,842 B2 | 7/2010 | Glukhovsky et al. | |
| 8,194,121 B2 | 6/2012 | Blumzvig et al. | |
| 8,194,122 B2 | 6/2012 | Amling et al. | |
| 8,465,421 B2 | 6/2013 | Finkman et al. | |
| 8,599,250 B2 | 12/2013 | Amling et al. | |
| 8,723,936 B2 | 5/2014 | Amling et al. | |
| 9,007,450 B2 | 4/2015 | Amling et al. | |
| 9,030,544 B2 | 5/2015 | Tashiro et al. | |
| 9,033,870 B2 | 5/2015 | Farr et al. | |
| 9,179,831 B2* | 11/2015 | McGrail | A61B 1/00105 |
| 9,386,914 B2 | 7/2016 | Birnkrant et al. | |
| 9,861,334 B2 | 1/2018 | Tajima et al. | |
| 11,265,450 B2 | 3/2022 | Katsuki | |
| 2003/0195390 A1 | 10/2003 | Graumann | |
| 2003/0228553 A1 | 12/2003 | Mandelkern et al. | |
| 2004/0243448 A1 | 12/2004 | Shoji et al. | |
| 2006/0116667 A1 | 6/2006 | Hamel et al. | |
| 2007/0162095 A1 | 7/2007 | Kimmel et al. | |
| 2007/0195539 A1 | 8/2007 | Birnkrant | |
| 2008/0139881 A1 | 6/2008 | Cover et al. | |
| 2008/0214896 A1 | 9/2008 | Krupa et al. | |
| 2009/0076331 A1 | 3/2009 | Konwitz et al. | |
| 2009/0247824 A1 | 10/2009 | Kawasaki et al. | |
| 2009/0270679 A1 | 10/2009 | Hoeg et al. | |
| 2009/0318758 A1 | 12/2009 | Farr et al. | |
| 2010/0014174 A1 | 1/2010 | Togino | |
| 2010/0097453 A1 | 4/2010 | Endo et al. | |
| 2010/0141744 A1 | 6/2010 | Amling et al. | |
| 2010/0208054 A1 | 8/2010 | Farr | |
| 2011/0222746 A1 | 9/2011 | Kotula et al. | |
| 2011/0243116 A1 | 10/2011 | Endo et al. | |
| 2012/0134410 A1 | 5/2012 | Kawasaki et al. | |
| 2012/0162472 A1 | 6/2012 | Amling et al. | |
| 2012/0209071 A1 | 8/2012 | Bayer et al. | |
| 2012/0246374 A1 | 9/2012 | Fino | |
| 2012/0289858 A1 | 11/2012 | Ouyang et al. | |
| 2013/0092173 A1 | 4/2013 | Alexander et al. | |
| 2013/0103907 A1 | 4/2013 | Katori et al. | |
| 2013/0204085 A1 | 8/2013 | Alexander et al. | |
| 2014/0003418 A1 | 1/2014 | Khait et al. | |
| 2014/0135576 A1 | 5/2014 | Hebert | |
| 2014/0275763 A1 | 9/2014 | King et al. | |
| 2015/0035967 A1 | 2/2015 | Wodnicki et al. | |
| 2015/0293877 A1* | 10/2015 | Liang | A61B 1/00016 710/33 |
| 2016/0000300 A1 | 1/2016 | Williams | |
| 2016/0048536 A1* | 2/2016 | Di | G06F 16/583 382/165 |
| 2016/0066770 A1 | 3/2016 | Barbato et al. | |
| 2016/0073855 A1 | 3/2016 | Farr et al. | |
| 2016/0213236 A1 | 7/2016 | Hruska et al. | |
| 2017/0095297 A1 | 4/2017 | Richmond et al. | |
| 2017/0209027 A1 | 7/2017 | Raj et al. | |
| 2017/0280988 A1 | 10/2017 | Barbato et al. | |
| 2017/0311777 A1 | 11/2017 | Hirayama et al. | |
| 2018/0084986 A1 | 3/2018 | Ochi et al. | |
| 2018/0220873 A1 | 8/2018 | Tani | |
| 2018/0296067 A1* | 10/2018 | Amling | A61B 1/00128 |
| 2018/0296289 A1 | 10/2018 | Rodriguez-Navarro et al. | |
| 2019/0052560 A1 | 2/2019 | Smith | |
| 2019/0104922 A1 | 4/2019 | Kasumi | |
| 2019/0133430 A1 | 5/2019 | Inglis et al. | |
| 2019/0142256 A1 | 5/2019 | Zhao et al. | |
| 2019/0200844 A1 | 7/2019 | Shelton et al. | |
| 2019/0238791 A1 | 8/2019 | Ingle | |
| 2019/0261844 A1 | 8/2019 | Walker et al. | |
| 2019/0313881 A1 | 10/2019 | Francher | |
| 2019/0320879 A1* | 10/2019 | Langell | A61B 1/07 |
| 2019/0335987 A1 | 11/2019 | Cook | |
| 2019/0350438 A1 | 11/2019 | Masuno et al. | |
| 2020/0113412 A1 | 4/2020 | Jensen | |
| 2020/0273575 A1 | 8/2020 | Wolf et al. | |
| 2020/0287899 A1 | 9/2020 | Koizumi et al. | |
| 2020/0305684 A1 | 10/2020 | Hagihara | |
| 2020/0405124 A1 | 12/2020 | Sonnenborg et al. | |
| 2021/0105467 A1 | 4/2021 | Tani | |
| 2021/0113059 A1 | 4/2021 | Kasumi | |
| 2021/0259522 A1 | 8/2021 | Ubbesen et al. | |
| 2021/0266435 A1 | 8/2021 | Katsuki | |
| 2021/0338040 A1 | 11/2021 | Michihata et al. | |
| 2022/0039634 A1 | 2/2022 | Williams | |
| 2022/0104822 A1 | 4/2022 | Shelton et al. | |
| 2022/0230643 A1* | 7/2022 | Pai | G10L 19/005 |
| 2023/0037178 A1 | 2/2023 | Kamon | |
| 2024/0108207 A1 | 4/2024 | Yazdi et al. | |

FOREIGN PATENT DOCUMENTS

| | | |
|---|---|---|
| EP | 2445210 A1 | 4/2012 |
| EP | 2286718 B1 | 12/2013 |
| EP | 2778999 A2 | 9/2014 |
| EP | 3417758 A1 | 12/2018 |
| EP | 3636133 A1 | 4/2020 |
| JP | 4918599 B2 | 4/2012 |
| JP | 2012-090974 A | 5/2012 |
| WO | 2008/063565 A2 | 5/2008 |
| WO | 2015/163942 A1 | 10/2015 |
| WO | 2019/198364 A1 | 10/2019 |
| WO | 2019/211938 A1 | 11/2019 |
| WO | 2020/031717 A1 | 2/2020 |
| WO | 2020/039716 A1 | 2/2020 |

OTHER PUBLICATIONS

Examination and Search Report for Denmark Application No. DK PA202170102, mailed on Jun. 21, 2021, 9 pages.

Examination and Search Report for Denmark Application No. PA202170098, mailed on May 18, 2021, 12 pages.

Examination and Search Report for Denmark Application No. PA202170099, mailed on Jun. 25, 2021, 8 pages.

Examination and Search Report for Denmark Application No. PA202170100, mailed on Jun. 25, 2021, 8 pages.

Examination and Search Report for Denmark Application No. PA202170101, mailed on Jun. 21, 2021, 9 pages.

International Search Report and Written Opinion received for PCT Patent Application No. PCT/EP2022/055139, mailed on Jun. 22, 2022, 14 pages.

International Search Report and Written Opinion received for PCT Patent Application No. PCT/EP2022/055133, mailed on Jun. 3, 2022, 10 pages.

International Search Report and Written Opinion received for PCT Patent Application No. PCT/EP2022/055134, mailed on Jul. 26, 2022, 14 pages.

International Search Report and Written Opinion received for PCT Patent Application No. PCT/EP2022/055135, mailed on Jun. 22, 2022, 9 pages.

International Search Report and Written Opinion received for PCT Patent Application No. PCT/EP2022/055136, mailed on Aug. 5, 2022, 17 pages.

Office Action in related U.S. Appl. No. 18/240,847 dated May 30, 2025, 28 pages.

Office Action in related U.S. Appl. No. 18/276,861 dated Aug. 1, 2025, 27 pages.

Office Action in related U.S. Appl. No. 18/277,303 dated Aug. 27, 2025, 32 pages.

(56) References Cited

OTHER PUBLICATIONS

Office Action in related U.S. Appl. No. 18/276,866 dated Jan. 16, 2026, 26 pages.
Office Action in related U.S. Appl. No. 18/277,303 dated Mar. 11, 2026, 30 pages.
Office Action in related U.S. Appl. No. 18/277,312 dated Dec. 17, 2025, 31 pages.

* cited by examiner

MEDICAL VISUALISATION DEVICE WITH WIRELESS TRANSMISSION

CROSS REFERENCE TO RELATED APPLICATIONS

This application is a National Phase entry under 35 U.S.C. § 371 of International Application No. PCT/EP2022/055133, filed Mar. 1, 2022, which claims the benefit of and priority from Danish Patent Application No. PA 2021 70098, filed Mar. 5, 2021. The foregoing applications are incorporated by reference herein in their entirety.

The present disclosure relates to a medical visualisation system and elements thereof. Particularly a medical visualisation system comprising a medical visualisation device and a monitor device, and wherein image data is wirelessly transmitted from the medical visualisation device and the monitor device.

BACKGROUND

Wireless medical devices that utilize wireless communication from a medical device to a processing device is known in the art.

However, these technical solutions are not widespread as commercially available products, and particularly they are not widespread when it comes to single use products. There exists a vast spectrum of technical solutions providing a wireless communication link, but few fulfil the needs for medical devices at hospital settings.

For instance, not all communication frequencies may be used at hospitals and for medical devices, and in particular visualisation devices, such as endoscopes, very low latency is an important parameter. Moreover, usability and cost are driving factors defining suitable technical solutions.

SUMMARY

The present disclosure relates to a visualisation device, such as an endoscope, and a visualisation system, such as an endoscope system. Particularly, but not exclusively the visualisation device may be a disposable camera endoscope. Alternatively, the visualisation device may be a video laryngoscope. The visualisation system may further comprise a monitor device for being connected to the visualisation device, e.g. the monitor device may be configured to receive image data from the visualisation device.

It is an object of the present disclosure to provide a solution which at least improve the solutions of the prior art. Particularly, it is an object of the present disclosure to provide a medical visualisation system and components thereof to enhance flexibility and usability of the system. For example, the present disclosure provides solutions for enabling wireless transmission of video data from a medical visualisation device, such as an endoscope or a laryngoscope, to a monitor device or other suitable equipment.

Accordingly, a medical visualisation system and elements thereof are disclosed. The medical visualisation system may comprise one or more or all of the elements disclosed in the following.

A medical visualisation device is disclosed. The medical visualisation system may comprise the medical visualisation device. The medical visualisation device may completely or partly be a single-use product. The medical visualisation device may be an endoscope. For example, the medical visualisation device may comprise a handle and an insertion tube extending from the handle to a distal tube portion. The handle may comprise a control button adapted to receive an input in a first input direction and/or in a second input direction. The touch input in the first input direction may cause a bendable section of the insertion tube to bend in a first bending direction. The touch input in the second input direction may cause the bendable section to bend in a second bending direction. Other examples of the medical visualisation device may be a laryngoscope or an endotracheal tube with integrated camera.

The medical visualisation device comprises an image sensor adapted to generate image data indicative of a view from the medical visualisation device and a light emitter adapted to provide illumination of the view. The view may be a view from the distal tube portion of the insertion tube. The light emitter may be an LED, an optical fibre, or similar element known to provide illumination. The medical visualisation device further comprises a device processing unit adapted to receive the image data from the image sensor and optionally encode the image data to provide encoded image data based on the image data. The device processing unit may comprise an image signal processor (ISP), a complex programmable logic device (CPLD), a field-programmable gate array (FPGA) and/or other suitable processing unit elements. The device processing unit may comprise memory, such as buffer memory.

The medical visualisation device comprises a device communication interface. For example, the medical visualisation device may comprise a device wireless communication module adapted to communicate with a monitor wireless communication module of a monitor device, such as the monitor device also disclosed herein. The device wireless communication module may be connected to the device processing unit. The device wireless communication module is adapted to receive the image data and/or the encoded image data from the device processing unit and transmit the image data and/or the encoded image data using a downstream data channel to the monitor wireless communication module.

Also disclosed is an auxiliary component. The medical visualisation system may comprise the auxiliary component. The auxiliary component may be couplable to a main device part to form the disclosed medical visualisation device, wherein the main device part comprises the image sensor and the light emitter and a main coupling part. The main device part may further comprise the handle and/or the insertion tube, as described above.

The auxiliary component may be couplable to the main device part. The auxiliary component comprises an auxiliary coupling part adapted to couple with the main coupling part. The auxiliary component further may comprise the device processing unit. The auxiliary component may further comprise one or more auxiliary communication interfaces. For example, the auxiliary component may comprise the device wireless communication module.

The main device part may be a single-use product. The auxiliary component may be a re-usable product. Hence, the auxiliary component may be adapted to be coupled to a plurality of main device parts.

The auxiliary component or part thereof may be a dongle for insertion into a designated receiver of the main device part. Alternatively or additionally, the auxiliary component or part thereof may be a wearable device, such as a wristwatch or an armband.

Also disclosed is a monitor device. The medical visualisation system may comprise the monitor device. The monitor device is operable to receive image data from a medical visualisation device, such as the disclosed medical visualisation device. The monitor device comprises a first housing. The medical visualisation system may comprise a display. The monitor device may comprise the display, e.g. accommodated in the first housing or couplable to the first housing, e.g. the display may be supported by the first housing or affixed to the first housing. Alternatively, the monitor device, such as the first housing, may be couplable to the display, e.g. the display may be an external display. For example, the monitor device may be devoid of a display. The display, whether forming part of the monitor device or not, may be a touch sensitive display.

The monitor device further comprises one or more monitor communication interfaces. For example, the monitor device may comprise a monitor wireless communication module adapted to communicate with a device wireless communication module of the medical visualisation device. The monitor wireless communication module may be adapted to receive image data and/or encoded image data using a downstream data channel from the device wireless communication module to the monitor wireless communication module.

The monitor device further comprises a monitor processing unit adapted to receive the image data and/or the encoded image data from the monitor wireless communication module, optionally decode the encoded image data, and cause the display to display a live representation of the image data. The monitor processing unit may comprise a complex programmable logic device (CPLD), a field-programmable gate array (FPGA) and/or other suitable processing unit elements. The monitor processing unit may comprise memory, such as buffer memory.

The monitor device may further comprise a monitor memory. The monitor memory may be connected to the monitor processing unit. The monitor processing unit may be adapted to read and/or write data from the monitor memory. The monitor memory may be any suitable electronic memory. The monitor memory may be non-volatile memory, such as a Flash memory.

The monitor wireless communication module may further be adapted to transmit settings data using an upstream data channel from the monitor wireless communication module to the device wireless communication module. The monitor processing unit may be adapted to provide and/or generate the settings data based on the image data to adjust settings of one or more components of the medical visualisation device, such as the light emitter and/or the image sensor of the medical visualisation device.

The device wireless communication module of the medical visualisation device and/or of the auxiliary component is further adapted to receive settings data using an upstream data channel from the monitor wireless communication module to the device wireless communication module.

The medical visualisation system may comprise a plurality of medical visualisation devices, e.g. comprising a first medical visualisation device and a second medical visualisation device, each of which may comprise some or all of the features as described in relation to the medical visualisation device disclosed herein. The plurality of medical visualisation devices may be different visualisation devices. In an example, the first medical visualisation device may be an endoscope comprising a flexible tube and the second medical visualisation device may be a video laryngoscope.

The plurality of medical visualisation devices may be different types, e.g. configured for different clinical purposes. For example, the first medical visualisation device may be a first device type configured for a first clinical purpose, and the second medical visualisation device may be a second device type configured for a second clinical purpose. An exemplary clinical purpose may be urology. For example, the first device type or the second device type may be a urology endoscope, such as a cystoscope or a ureteroscope. Another exemplary clinical purpose may be gastroenterology. For example, the first device type or the second device type may be a gastro-intestinal endoscope, such as a gastroscope, a duodenoscope or a colonoscope. Yet another exemplary clinical purpose may be pulmonology. For example, the first device type or the second device type may be a pulmonology endoscope, such as a bronchoscope.

The plurality of medical visualisation devices may comprise image sensors of same or different image sensor type. For example, the image sensor of the first medical visualisation device may be a first image sensor type and the image sensor of the second medical visualisation device may be a second image sensor type. Alternatively the image sensor of the second medical visualisation device may be the first image sensor type. Alternatively or additionally, the image sensor of a third medical visualisation device may be a third image sensor type or the second image sensor type. The image sensor types may differ on various aspects, e.g. by power supply voltage, by image resolution, by physical size etc.

The auxiliary component may be couplable to the plurality of medical visualisation devices, e.g. the auxiliary component may be couplable both to the first medical visualisation device and the second medical visualisation device and/or the third medical visualisation device. Hence, for example, one auxiliary component may be couplable to a range of different medical visualisation devices.

The present disclosure provides a solution for providing wireless transmission of video data from medical visualisation devices, such as an endoscope and/or laryngoscope, to a monitor device or other suitable equipment, which act to fulfil requirements for medical visualisation procedures, e.g. reduced latency and utilizing suitable communication bands for hospital settings. Furthermore, the present disclosure provides a solution which allows a monitor device or other related devices to adjust parameters of the visualisation device, e.g. by wireless data transfer, such that need for processing in a, possibly disposable, visualisation device is reduced.

It is a further advantage of the present disclosure that existing protocols and standard components may to a large degree be used, making it easier to implement, and reducing manufacturing costs, which is of particular relevance for disposable devices.

BRIEF DESCRIPTION OF THE FIGURES

Embodiments of the disclosure will be described in more detail in the following with regard to the accompanying figures. The figures show one way of implementing the present disclosure and are not to be construed as being limiting to other possible embodiments falling within the scope of the attached claim set.

DETAILED DESCRIPTION

Figure 1A:
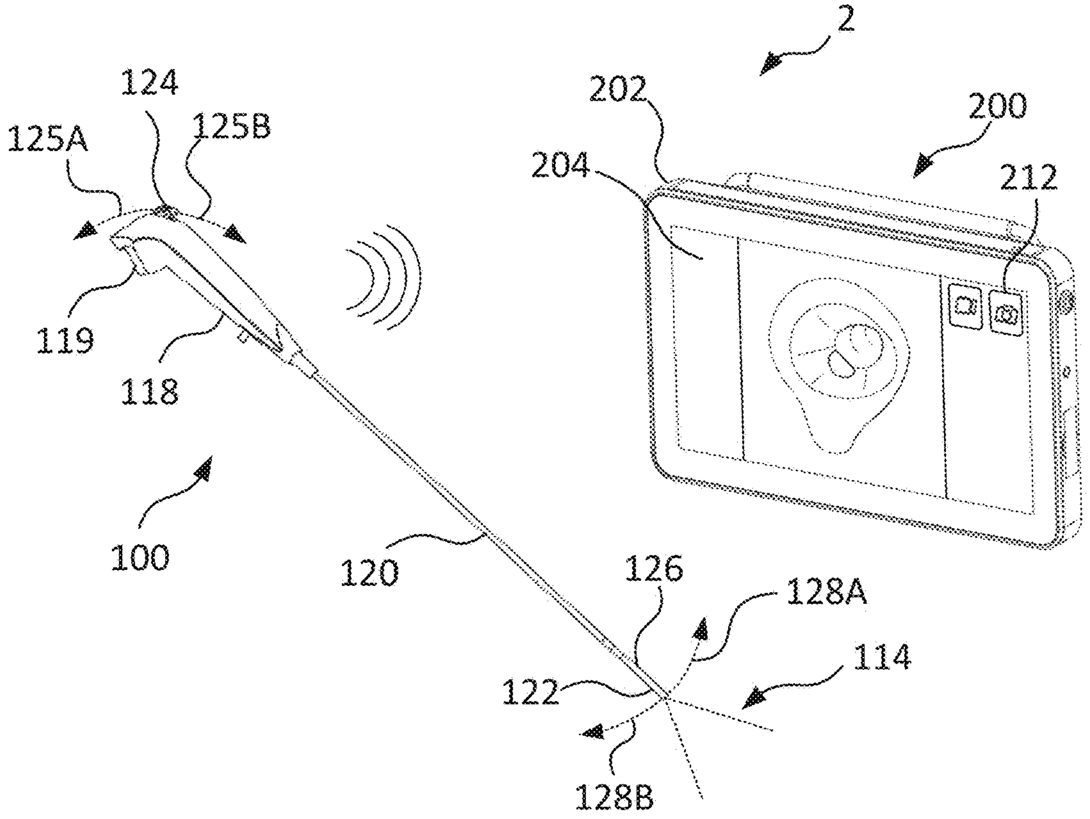
FIG. 1 schematically illustrates an exemplary medical visualisation system.

Further details of the aspects of the disclosure, as set out above, are provided in the following. Details and/or advantages may be practiced in any embodiment and/or aspect even if not so illustrated, or if not so explicitly described.

The upstream data channel from the monitor wireless communication module to the device wireless communication module may have a limited bandwidth compared to the downstream data channel from the device wireless communication module to the monitor wireless communication module. The upstream data channel may have a maximum transmission capacity of or be limited to less than 500 bits per second, such as less than 250 bits per second, such as less than 100 bits per second, such as less than 80 bits per second. The downstream data channel may be able to transmit more than 4 Gbits per second, such as more than 10 Gbits per second, such as more than 15 Gbits per second, such as more than 20 Gbits per second, such as more than 25 Gbits per second.

The device wireless communication module may comprise a plurality of device wireless communication submodules and/or the monitor wireless communication module may comprise a plurality of monitor wireless communication submodules. Each of the plurality of monitor communication submodules may be adapted to communicate with a respective device wireless communication submodule of the plurality of monitor wireless communication submodules. Thus, the downstream data channel may comprise a plurality of downstream data sub channels and/or the upstream data channel may comprise a plurality of upstream data sub channels. Hence, the bandwidth available for the downstream data channel and/or the upstream data channel may be increased by adding more device wireless communication submodules to the device wireless communication module and/or by adding more monitor wireless communication submodules to the monitor wireless communication module.

The settings data transmitted using the upstream data channel may be indicative of adjustments for one or more components, e.g. the light emitter and/or the image sensor, of the medical visualisation device. For example, the monitor processing unit may be adapted to provide and/or generate the settings data based on the image data to adjust settings of one or more components to enhance quality of the images.

The device processing unit of the medical visualisation device and/or of the auxiliary component may be adapted to receive the settings data from the device wireless communication module and adjust settings of the one or more components, e.g. the light emitter and/or the image sensor, of the medical visualisation device based on the settings data. For example, the device processing unit may be adapted to adjust settings of the image sensor, e.g. including colour, contrast, gain, and/or exposure settings, based on the settings data. Alternatively or additionally, the device processing unit may be adapted to adjust settings of the light emitter, e.g. including current, brightness and/or PWM settings.

The communication between the device wireless communication module and the monitor wireless communication module may be in accordance with a standard wireless specification. For example, the communication between the device wireless communication module and the monitor wireless communication module may be in accordance with the Wireless HD (WiHD) specification and/or the Wireless Gigabit Alliance (WiGig) specification. The device wireless communication module and the monitor wireless communication module may be adapted accordingly. For example, the device wireless communication module and/or the monitor wireless communication module may be a Wireless HD chipset and/or a Wireless Gigabit Alliance chipset.

The image data may have a first resolution, such as 400×400 pixels, or at least 400×400 pixel, such as 800×800 pixels, or at least 800×800 pixels, and may be generated at a first frame rate, such as 30 frames per second, or at least 30 frames per second, such as 60 frames per second, or at least 60 frames per second.

The device processing unit may receive the image data from the image sensor and encode the image data to encoded image data. For example, such as to allow wireless transmission of the image data in accordance with a wireless specification. The encoded image data may use a format with a total number of bits, such as 24 bits. A first portion of the total number of bits may be used to encode the image data. The first portion of the total number of bits may be less than the total number of bits. For example, the first portion of the first number of bits may be 10 bits. A second portion of the total number of bits may be used to embed additional information, such as battery status or settings information in the encoded image data.

The device wireless communication module and/or the monitor wireless communication module may be adapted to communicate wirelessly, such as to wirelessly receive and/or wirelessly transmit data, e.g. image data, encoded image data and/or other data described herein. The device wireless communication module and/or the monitor wireless communication module may be adapted to communicate using a radio frequency of more than 10 GHz, such as using a radio frequency between 57-66 GHz, such as between 57-64 GHz, such as between 57.05-64 GHz, such as between 59-64 GHz, such as between 59.4-63.56, such as between 59.4-62.9 GHz. These frequencies facilitate high bandwidth and low latency for the live images to be displayed on the display. Furthermore, the exemplary frequencies have a limited range making it advantageous to use for medical visualisation procedures, as this lowers the risk of the image data being interceptable or interfering with other procedures outside the room wherein the procedure is being performed.

The device wireless communication module may comprise a device antenna. The device antenna may be enclosed in a housing of the medical visualisation device and/or of the auxiliary component, such as an auxiliary housing of the auxiliary component. Alternatively, the device antenna may form part of the housing of the medical visualisation device and/or of the auxiliary component. Alternatively, the device antenna may extend external of the housing of the medical visualisation device and/or of the auxiliary component. The device antenna may be positioned at a distance from the housing of the medical visualisation device and/or of the auxiliary component, e.g. of more than 0.5 meters, and/or the device antenna may be adapted to be positioned near or at the head of an operator of the medical visualisation device.

The medical visualisation device and/or the auxiliary component may comprise a battery, e.g. a rechargeable battery, e.g. a Li-Ion battery, adapted to power the medical visualisation device. For example, the battery may be adapted to power the light emitter, the image sensor, the device processing unit and/or the device wireless communication module. The battery may be provided in the auxiliary component. The battery may, when fully charged, comprise a battery capacity allowing at least 2 hours of continued usage of the medical visualisation device.

The medical visualisation device, such as the main device part, such as the main coupling part of the main device part, may comprise a safety-circuit. The safety circuit may be adapted to prevent excessive current to elements of the medical visualisation device, such as the light emitter and/or the image sensor.

The medical visualisation device, such as the main device part, such as the main coupling part of the main device part, may comprise a device identifier comprising device identifier information, e.g. to allow identification of the medical visualisation device, e.g. including serial number, batch number, device type, etc. The device processing unit may be adapted to obtain the device identifier information from the device identifier. The device processing unit and/or the monitor processing unit may be adapted to configure the auxiliary component and/or the monitor device to be configured according to the obtained device identifier information, e.g. such as to be compatible with the medical visualisation device and/or the main device part.

The device identifier may include an electronically readable memory, such as an EPROM, RFID, NFC or similar. In other examples the device identifier may be a QR-code, bar-code or similar. The device identifier, or the electronically readable memory of the device identifier, may be connectable by one or more terminals. Alternatively, the device identifier may be readable without the necessity to establish an electrical contact. For example, the device identifier may be readable by means of a short-range communication circuit, such as an RFID or NFC circuit.

Providing the medical visualisation device and/or the main device part with a safety circuit and/or a device identifier facilitates that the auxiliary component and/or the monitor device may be used with different devices, e.g. gastroscopes, bronchoscopes, laryngoscopes etc, and/or devices comprising different electronics, such as different image sensors.

The monitor wireless communication module may comprise a monitor antenna. The monitor antenna may be positioned external to a housing of the monitor device, such as the first housing. The monitor antenna may be adapted to be positioned at a distance from the housing of the monitor device of more than 1 meter, such as more than 2 meters. The monitor antenna may be adapted to be positioned above an operating setting in an operating room, such as at the ceiling of the operating room. The monitor antenna may be positioned above the first housing. The monitor antenna may be wired to a housing of the monitor device, such as the first housing. Positioning the monitor antenna external to the housing of the monitor device, at a distance from the housing, and/or at the ceiling of an operating room, increases the likelihood of line of sight between the device antenna of the device wireless communication module and the monitor antenna, facilitating uninterrupted transmission of image data. Especially for wireless communication utilizing very high radio frequencies, e.g. above 10 GHz, such as between 57-66 GHz, obstacles between transmitter and receiver have a high likelihood of influencing the data transfer. The monitor antenna and the device antenna may be positioned with line of sight there between.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1*a* schematically illustrates an exemplary medical visualisation system 2 comprising an exemplary medical visualisation device 100 and an exemplary monitor device 200. In the illustrated example, the medical visualisation device 100 is an endoscope, such as a bronchoscope. In other examples, the medical visualisation device of the medical visualisation system may be a laryngoscope, a gastro-intestinal endoscope, a urology endoscope, etc.

The medical visualisation device 100 comprises a handle 118, and, in the illustrated example, the medical visualisation device 100 comprises an insertion tube 120 extending from the handle 118 to a distal tube portion 122. The handle may, as illustrated, comprise a control button 124 and the insertion tube 120 may comprise a bendable section 126. The control button 124 is adapted to receive an input in a first input direction 125A and in a second input direction 126B. The bendable section 126 is adapted to bend accordingly in a first bending direction 128A and a second bending direction 128B. A touch input in the first input direction 125A causes the bendable section 126 to bend in the first bending direction 128A. A touch input in the second input direction 125B causes the bendable section 126 to bend in the second bending direction 128B.

The medical visualisation device 100 has an image sensor adapted to generate image data indicative of a view 114 from the visualisation device. As illustrated, the view 114 from the visualisation device 100 may be from the distal tube portion 122 of the insertion tube 120. The medical visualisation device 100 further comprises a light emitter adapted to provide illumination of the view 114.

The medical visualisation device 100 and the monitor device 200 are adapted to communicate wirelessly. For example, the medical visualisation device 100 is adapted to transmit image data using a downstream data channel from the medical visualisation device 100 to the monitor device 200. Alternatively or additionally, the medical visualisation device may be adapted to receive settings data using an upstream data channel from the monitor device 200 to the medical visualisation device 100.

The monitor device 200 comprises a first housing 202. In the illustrated example, the monitor device 200 further comprises a display 204 accommodated in the first housing 202. In alternative examples, the monitor device 200, such as the first housing 202 of the monitor device 200, may be coupled to an external display (see FIG. 1*b*). The monitor device 200 is operable to receive image data from a medical visualisation device 100 and display on the display a live representation of the image data indicative of the view 114 from the visualisation device 100. The display 204 may be a touch sensitive display.

The monitor device 200 may be adapted to wirelessly communicate with the medical visualisation device 100. For example, the monitor device 200 may be adapted to receive image data using the downstream data channel from the medical visualisation device 100 to the monitor device 200. The monitor device 200 may further be adapted to transmit settings data using an upstream data channel from the monitor device 200 to the medical visualisation device 100. Such settings data may, for example, be used to adjust brightness of the light emitter or control colour, contrast, gain and/or exposure settings of the image sensor. These settings may be adaptively adjusted based on the received image data, e.g. to adjust under/over exposure or similar.

The medical visualisation system 2 may be operable to store an image data file and/or a video sequence file in response to receipt of a user input signal indicative of a user activating an image capture button 119, 212. The image capture button may be a device button 119 on the medical visualisation device 100, and/or a monitor button 212 on the monitor device 200, e.g. a soft button displayed on the display 204.

Figure 1B:
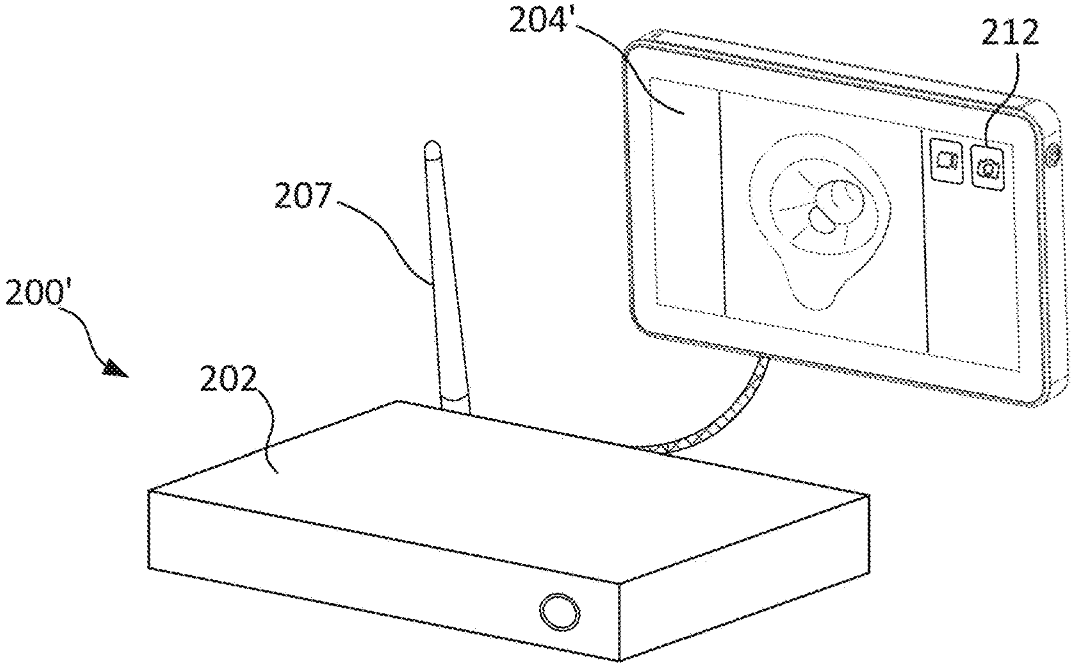

FIG. 1*b* schematically illustrates a monitor device 200' comprising a first housing 202, wherein the monitor device 200, such as the first housing 202, may be coupled to an external display 204'. The external display 204' may be a touch sensitive display. Other than the display 204' being external to the first housing 202, the monitor device 200' may be similar and comprise the same functionality as the monitor device 200. For example, the monitor device 200' is operable to receive image data from a medical visualisation device 100 (FIG. 1*a*) and display on the display 204' a live representation of the image data indicative of the view 114 from the visualisation device 100.

The monitor device 200' may be adapted to wirelessly communicate with the medical visualisation device 100. For example, the monitor device 200' may be adapted to receive image data using the downstream data channel from the medical visualisation device 100 to the monitor device 200'. The monitor device 200' may further be adapted to transmit settings data using an upstream data channel from the monitor device 200' to the medical visualisation device 100.

It is emphasized that the monitor device 200, as illustrated in the following examples may be substituted by the monitor device 200', as illustrated in FIG. 1*b*.

Figure 2:
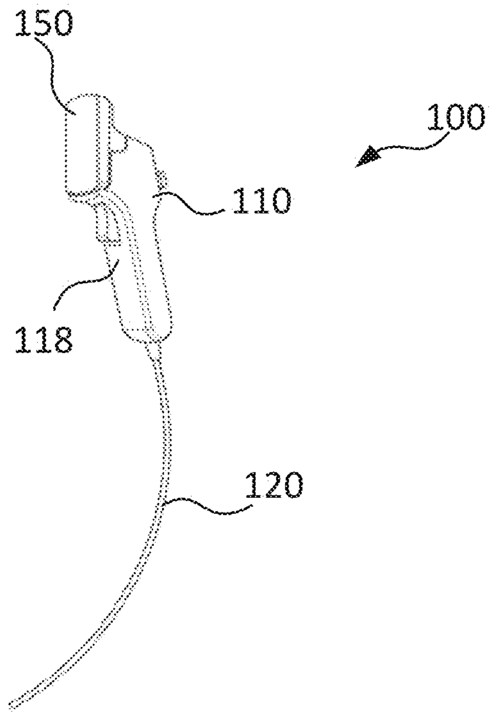
FIG. 2 schematically illustrates an exemplary medical visualisation device.

FIG. 2 schematically illustrates an exemplary medical visualisation device 100, such as the medical visualisation device 100 as described with respect to FIG. 1*a*.

The medical visualisation device 100 of FIG. 2 further comprises an auxiliary component 150 couplable to a main device part 110 of the medical visualisation device 100. The main device part 110 comprises the handle 118 and the insertion tube 120, as described with respect to FIG. 1*a*. The auxiliary component 150 comprises various electronic components, e.g. for establishing wireless communication with the monitor device.

The auxiliary component 150 may be adapted to be used multiple times, e.g. being reusable, while the man device part 110 may be configured as a single-use product, e.g. being disposable. By providing electronic components in a reusable component while the main device part being in direct contact with the patient being disposable, valuable resources may be preserved and costs may be lowered, while observing increased patient safety and reduced risk of cross contamination.

Figure 3A:
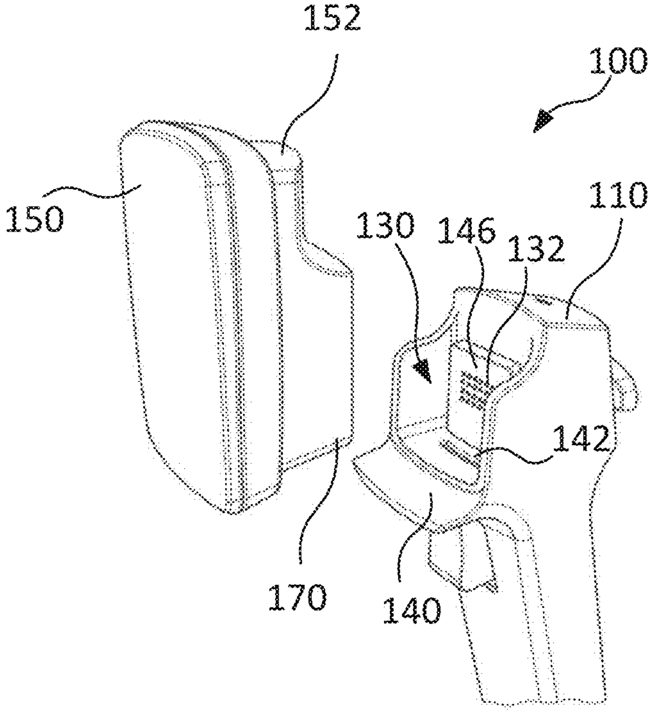
FIGS. 3*a* and 3*b* schematically illustrate the medical visualisation device.
Figure 3B:
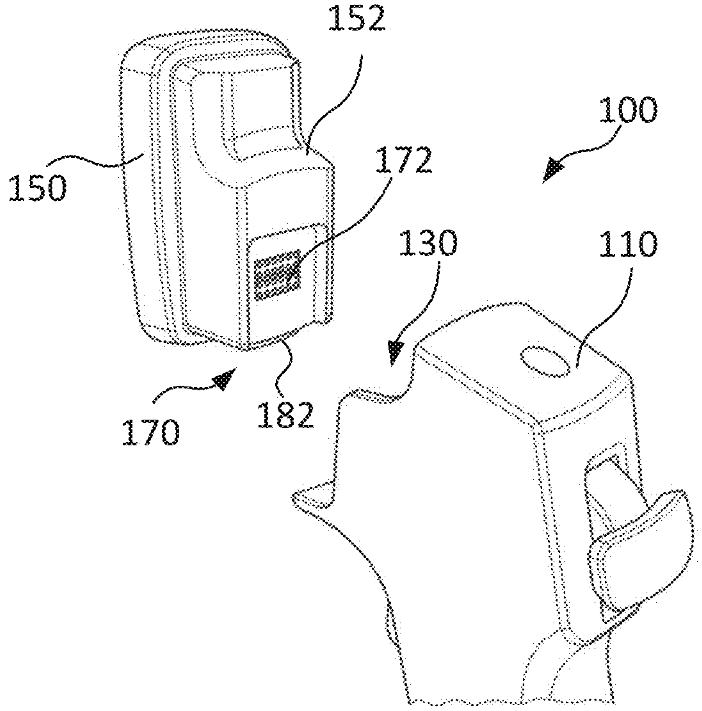

FIGS. 3*a* and 3*b* schematically illustrate the medical visualisation device 100, as also illustrated in FIG. 2, wherein the auxiliary component 150 is detached from the main device part 110.

The auxiliary component 150 comprises an auxiliary housing. The auxiliary housing 152 may be fluid-tight to the outside such that the auxiliary component 150 is adapted for wet cleaning, e.g. by immersion in a liquid. For example, the auxiliary housing 152 may be surface coated with a sealing liquid, e.g. by immersion in the sealing liquid, to make the auxiliary housing 152 fluid-tight. Alternatively or additionally, terminals of the auxiliary component 150 may be provided by insert moulding.

The main device part 110 comprises a main coupling part 130. The auxiliary component 150 comprises an auxiliary coupling part 170. The auxiliary coupling part 170 and the main coupling part 150 are adapted to be coupled. The main coupling part 130 is adapted to couple with the auxiliary coupling part 170. The auxiliary coupling part 170 is adapted to couple with the main coupling part 130.

The main coupling part 130 comprises one or more main terminals 132. The one or more main terminals 132 may be electrically connected to a light emitter and an image sensor of the main device part 110.

The auxiliary coupling part 170 comprises one or more auxiliary terminals 172. The one or more auxiliary terminals 172 and the one or more main terminals 132 are adapted to connect, when the auxiliary coupling part 170 is coupled with the main coupling part 130. The one or more auxiliary terminals 172 are adapted to connect to the one or more main terminals 132. The one or more main terminals 132 are adapted to connect to the one or more auxiliary terminals 172.

The main coupling part 130 has a main surface 140 with a main primary engagement member 142. The main primary engagement member 142 may be a recess, as illustrated. Alternatively, the main primary engagement member 142 may be a protrusion. The main primary engagement member 142 may be another suitable engagement member.

The auxiliary coupling part 170 has an auxiliary primary engagement member 182 adapted to engage with the main primary engagement member 142, such as to restrict movement of the auxiliary primary engagement member 182 along the main surface 140. For example, the auxiliary primary engagement member 182 may be a cooperating member of the main primary engagement member 142. For example, the auxiliary primary engagement member 182 may be a protrusion, as illustrated. Alternatively, the auxiliary primary engagement member 182 may be a recess. The auxiliary primary engagement member 182 may be another suitable engagement member.

The main coupling part 130 comprise a primary surface 146. The primary surface 146 accommodates exposed portions of the one or more main terminals 132. The primary surface 146 may be substantially perpendicular to the main surface 140, as illustrated.

The main coupling part 130 may have a main secondary engagement member, and the auxiliary coupling part may have an auxiliary secondary engagement member adapted to engage with the main secondary engagement member, such as to restrict movement of the auxiliary secondary engagement member perpendicular to the main surface 140. The primary surface 146 may be between the main primary engagement member 142 and the main secondary engagement member.

Figure 4:
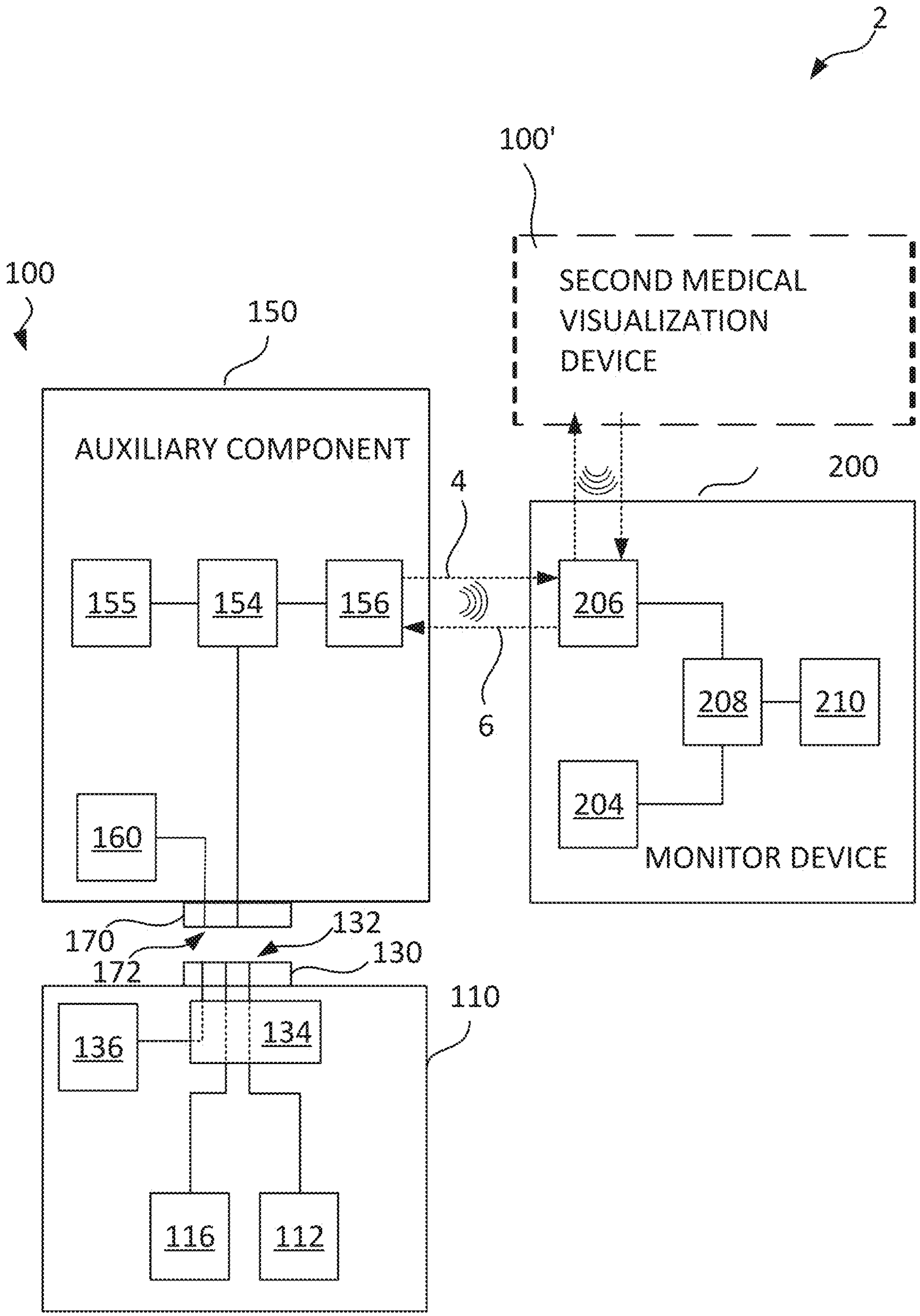
FIG. 4 is a block diagram schematically illustrating a medical visualisation system, FIG. 5 schematically illustrates an exemplary operating room.

FIG. 4 is a block diagram schematically illustrating a medical visualisation system 2, such as the medical visualisation system 2 as described with respect to previous figures.

The medical visualisation system 2 comprises an exemplary medical visualisation device 100, such as the medical visualisation device 100 as described with respect to previous figures, and an exemplary monitor device 200, such as the monitor device 200 as described with respect to previous figures.

The medical visualisation device 100, as the medical visualisation device 100 of FIGS. 2 and 3, comprises a main device part 110 and an auxiliary component 150 couplable to the main device part 110.

The main device part 110 comprises an image sensor 112 adapted to generate image data indicative of a view from the main device part 110, a light emitter 116 adapted to provide illumination of the view, and a main coupling part 130 having one or more main terminals 132 electrically connected to the light emitter 116 and the image sensor 112. The main device part 110 may further comprise a safety circuit 134 and a device identifier 136.

The device identifier 136 may comprise device identifier information, such as serial number of the main device part 110, which may uniquely identify the main device part 110. Also, the device identifier information may be indicative of the type of visualisation device, e.g. whether the medical visualisation device 100 and/or the main device part 110 is a bronchoscope or a laryngoscope. Alternatively or additionally, the device identifier information may be indicative of the brand of the visualisation device, production version, batch number etc.

The device identifier 136 may include an electronically readable memory, such as an EPROM, RFID, NFC or similar. In other examples the device identifier may be a QR-code, bar-code or similar. The device identifier 136 may be connected to the one or more main terminals 132, as illustrated. However, in other exemplary medical visualisation devices, the device identifier 136 may be readable without the necessity to establish an electrical contact. For example, the device identifier 136 may be readable by means of a short-range communication circuit, such as an RFID or NFC circuit. In other exemplary medical visualisation devices, the device identifier 136 may be optically read, e.g. wherein the device identifier is a QR-code or bar code.

The auxiliary component 150 comprises an auxiliary coupling part 170 adapted to couple with the main coupling part 130. The auxiliary coupling part 170 comprises one or more auxiliary terminals 172 adapted to connect to the one or more main terminals 132 of the main coupling part 130, when the auxiliary coupling part 170 is coupled with the main coupling part 130.

The auxiliary component 150 comprises a device processing unit 154 and a device wireless communication module 156. The auxiliary component 150 may further comprise an auxiliary memory 155, such as a flash memory or other suitable electronic memory. The device processing unit 154 may be adapted to read and/or write to/from the auxiliary memory 155. The auxiliary component 150 may further comprise a battery 160, as illustrated. The battery 160 may be a rechargeable battery.

The device processing unit 154 is electrically connected to the one or more auxiliary terminals 172 and adapted to receive the image data from the image sensor 112, when the auxiliary component 150 is coupled to the main device part 110. The device processing unit 154 may further be adapted to encode the image data to provide encoded image data based on the image data and transmit the image data and/or the encoded image data to the device wireless communication module 156, for wireless transmission to the monitor device 200. For example, the device processing unit 154 may encode the image data in accordance with a wireless video transmission protocol.

The device wireless communication module 156 is connected to the device processing unit 154 and adapted to communicate with a monitor wireless communication module 206 of the monitor device 200. The device wireless communication module 156 is adapted to receive the image data and/or the encoded image data from the device processing unit 154 and transmit the image data and/or the encoded image data using a downstream data channel 4 to the monitor wireless communication module.

The device processing 154 unit may be adapted to obtain the device identifier information from the device identifier 136, e.g. via the one or more auxiliary terminals 172 and one or more main terminals 132.

The battery 160 is adapted to power the medical visualisation device 100. The battery 160 is adapted to power the electronic elements of the auxiliary component 150, such as the device processing unit 154 and/or the device wireless communication module. For example, the battery 160 may be connected to the electronic components of the auxiliary component 150, e.g. the device processing unit 154 and/or the device wireless communication module. The battery 160 is electrically connected to the one or more auxiliary terminals 172, such as to power the main device part 110 and/or the electronic elements thereof, when the auxiliary component 150 is coupled to the main device part 110, such as when the main coupling part 130 is coupled with the auxiliary coupling part 170. For example, the battery 160 may be adapted to power the image sensor 112 and light emitter 114 of the main device part 110. The battery 160 may be adapted to power the device identifier 136.

The safety circuit 134 may be adapted to prevent excessive current to the elements of the main device part 110, such as the light emitter 116, the image sensor 112 and/or the device identifier 136. For example, the one or more main terminals 132 may be electrically connected to the light emitter 116, the image sensor 112 and/or the device identifier 136 via the safety circuit. Thereby, the elements of the main device part 110 may be protected, in case an auxiliary component able to power another, more power consumptive, device part, is coupled to the main device part 110.

The monitor device 200 comprises the monitor wireless communication module 206 and a monitor processing unit 208. The monitor device 200 may comprise a monitor memory 210, such as a Flash memory or other suitable electronic memory.

The monitor device 200 may further comprise a display 204, as illustrated. In an alternative example, such as exemplified for the monitor device 200' in FIG. 1*b*, the monitor device may be couplable to an external display. In either case, the display 204 may be operable to display a live representation of the image data indicative of the view 114 from the visualisation device 100. The display 204 may be touch sensitive display.

The monitor wireless communication module 206 is adapted to communicate with the device wireless communication module 156. The monitor wireless communication module 206 is adapted to receive image data and/or encoded image data using the downstream data channel 4 from the device wireless communication module 156 to the monitor wireless communication module 206. The monitor wireless communication module 206 may further be adapted to transmit the received image data and/or encoded image data to the monitor processing unit 208.

The monitor processing unit 208 is adapted to receive the image data and/or the encoded image data from the monitor wireless communication module 206. The monitor processing unit 208 may further be adapted to decode the encoded image data. The monitor processing unit 208 may be adapted to cause the display 204 to display a live representation of the image data.

The monitor wireless communication module 206 may further be adapted to transmit settings data using an upstream data channel 6 from the monitor wireless communication module 206 to the device wireless communication module 156. The device wireless communication module 156 is adapted to receive settings data using the upstream data channel 6.

The monitor processing unit 208 may be adapted to generate and/or provide the settings data to the monitor wireless communication module 206 for transmission to the medical visualisation device. For example, the monitor processing unit 208 may generate the settings data based on the image data, e.g. to adjust settings of one or more components of the medical visualisation device 100, e.g. the light emitter 116 and/or the image sensor 112. The device processing unit 154 may be adapted to receive the settings data from the device wireless communication module 156 and adjust settings of one or more components of the medical visualisation device 100 based on the settings data. For example, the settings data may be indicative of adjustment of the image sensor, e.g. including colour, contrast, gain, and/or exposure settings. Alternatively or additionally, the settings data may be indicative of adjustment of the light emitter, e.g. including current, brightness, and/or PWM settings. By utilizing the upstream data channel 6 to transmit settings data, the monitor processing unit 208 may process the image data received and continuously adjust settings of the light emitter 116 and/or image sensor 112, to enhance the image quality. Thereby, the heavier computational image analysis may be performed in the monitor device 200, allowing the medical visualisation device 100 to draw less power, needing less battery capacity and effectively allowing the medical visualisation device to be lighter and more compact.

The wireless communication between the medical visualisation device 100 and the monitor device 200 may be established by activation of a pairing sequence, e.g. by the user pressing a pairing button on the monitor device 200 and on the medical visualisation device 100. In response to activation of the pairing sequence, the device processing unit 154 and the monitor processing unit 208 cause the device wireless communication module 156 and the monitor wireless communication module 206 to exchange information to setup a data link for subsequent data transfer, e.g. including information regarding communication channel for the data link, identification details of the respective devices, etc.

After establishing the data link, an initialisation sequence may be performed. Alternatively, the initialisation sequence may be performed in response to the auxiliary component 150 and the main device part 110 being coupled. The initialisation sequence may include that the monitor processing unit 208 receives device identifier information from the device identifier 136. Based on the device identifier information, the monitor processing unit 208 is able to process the image data received from the medical visualisation device 100. Based on the device identifier information, the monitor processing unit 208 may generate and/or provide initial settings data to the monitor wireless communication module 206 for transmission to the medical visualisation device 100, such as to the device processing unit 154, which may adjust settings of one or more components of the medical visualisation device 100 based on the initial settings data. Thereby, the settings of the one or more components may be set to a default or initial value, which may be dependent on various information related to the specific device, i.e. based on the device identifier information. Similar to the settings data, explained above, the initial settings data may be indicative of adjustment of the image sensor, e.g. including colour, contrast, gain, and/or exposure settings. Alternatively or additionally, the initial settings data, like the settings data, may be indicative of adjustment of the light emitter, e.g. including current, brightness, and/or PWM settings.

The initialisation sequence may further include that a designated user interface is loaded on the monitor device 200. For example, a designated user interface may be loaded based on the device identifier information, e.g. depending on whether the medical visualisation device 100 and/or the main device part 110 is a bronchoscope, a laryngoscope, or another visualisation device.

Further, FIG. 4 also illustrates that the medical visualisation system 2 may comprise a plurality of medical visualisation devices, e.g. the first medical visualisation device 100 as already described and a second medical visualisation device 100'. The second medical visualisation device 100' may generally comprise the similar features and components as the first medical visualisation device 100 and is therefore, for brevity, not described in further details. As seen the monitor device 200, such as the monitor wireless communication module 206 may be adapted to communicate with the second medical visualisation device 100', such as with a device wireless communication module of the second medical visualisation device 100'. For example, the monitor wireless communication module 206 may be adapted to receive image data and/or encoded image data using a downstream data channel from the second medical visualisation device 100'. The monitor processing unit 208 may be adapted to cause the display 204 to display a live representation of the image data of the second medical visualisation device 100', e.g. simultaneously with display of the image data of the first medical visualisation device 100, e.g. side by side or picture-in-picture, or in another arrangement.

The monitor wireless communication module 206 may further be adapted to transmit settings data using an upstream data channel from the monitor wireless communication module 206 to the second medical visualisation device 100', such as to a device wireless communication module of the second medical visualisation device, as similarly described with respect to the medical visualisation device 100.

Figure 5:
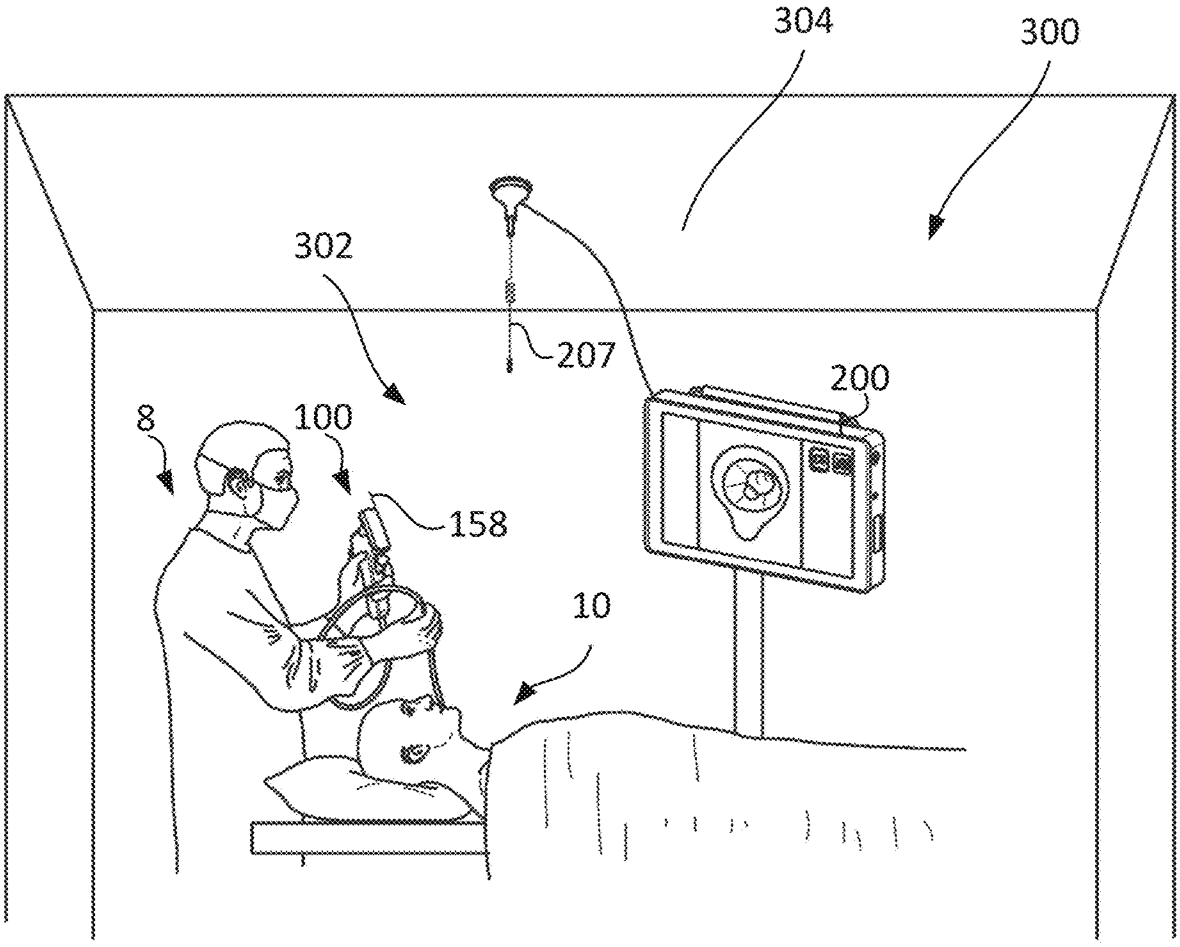

FIG. 5 schematically illustrates an exemplary operating room 300 with an operating setting 302, wherein an endoscope procedure is being performed on a patient 10 by an operator 8 of a medical visualisation device 100. The operator 8 is seeing the view from the medical visualisation device 100 at the monitor device 200.

The monitor wireless communication module of the monitor device 200 comprises a monitor antenna 207, and the device wireless communication module of the medical visualisation device 100 comprises a device antenna 158. Here the device antenna 158 is shown for the purpose of illustration, alternatively, the device antenna 158 may be positioned inside a housing of the medical visualisation device 100.

The image data from the medical visualisation device 100 is transmitted to the monitor device by wireless communication via the device antenna 158 and the monitor antenna 207. To ensure constant wireless transfer of the image data, it may be advantageous to ensure or promote line of sight between the device antenna 158 and the monitor antenna 207. Therefore, the monitor antenna 207 is positioned external to a housing of the monitor 200. The monitor antenna 207 may be positioned at a distance from the housing, e.g.

of more than 2 meters. The monitor antenna 207 may be adapted to be positioned above the operating setting 302, such as at the ceiling 304 of the operating room 300, as illustrated.

Figure 6:
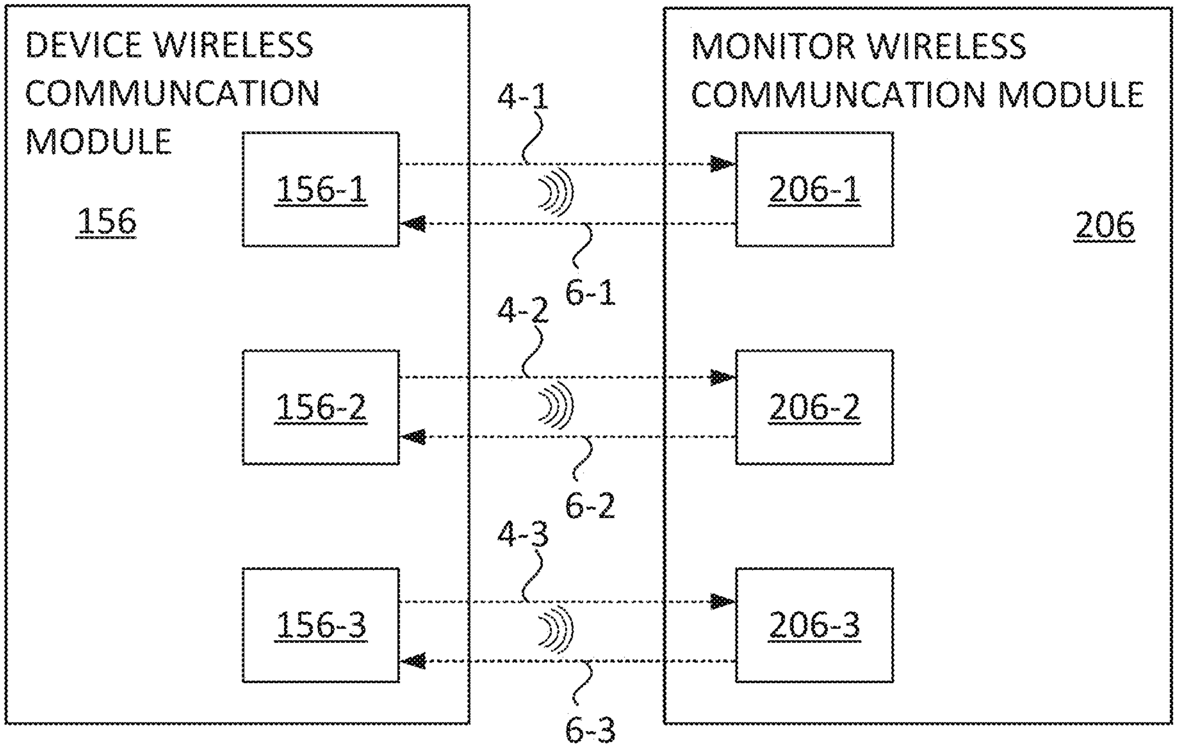
FIG. 6 is a block diagram schematically illustrating examples of wireless communication modules.

FIG. 6 is a block diagram schematically illustrating examples of the device wireless communication module 156 and the monitor wireless communication module 206, wherein the device wireless communication module comprises a plurality of device wireless communication submodules 156-1, 156-2, 156-3 (in this case three device wireless communication submodules), and wherein the monitor wireless communication module 206 comprises a plurality of monitor wireless communication submodules 206-1, 206-2, 206-3 (in this case three monitor wireless communication submodules). Each of the monitor communication submodules 156-1, 156-2, 156-3 communicates with a respective device wireless communication submodule 206-1, 206-2, 206-3. Thereby, the device wireless communication module 156 and the monitor wireless communication module 206 may communicate with a plurality of downstream data sub channels 4-1, 4-2, 4-3 collectively forming the downstream data channel 4 of FIG. 4, and a plurality of upstream data sub channels 6-1, 6-2, 6-3 collectively forming the upstream data channel 6 of FIG. 4.

Exemplary embodiments of the present disclosure are set out in the following items:

1. A medical visualisation device having:
   - an image sensor adapted to generate image data indicative of a view from the medical visualisation device,
   - a light emitter adapted to provide illumination of the view,
   - a device processing unit adapted to receive the image data from the image sensor and encode the image data to provide encoded image data based on the image data,
   - a device wireless communication module adapted to communicate with a monitor wireless communication module of a monitor device, the device wireless communication module being adapted to receive the encoded image data from the device processing unit and transmit the encoded image data using a downstream data channel from the device wireless communication module to the monitor wireless communication module, and wherein the device wireless communication module is adapted to receive settings data using an upstream data channel from the monitor wireless communication module to the device wireless communication module.

2. Medical visualisation device according to item 1, wherein the upstream data channel is limited to less than 500 bits per second, such as less than 250 bits per second, such as less than 100 bits per second, such as less than 80 bits per second.

3. Medical visualisation device according to any of the preceding items, wherein the device processing unit is adapted to receive the settings data from the device wireless communication module and adjust settings of one or more components of the medical visualisation device based on the settings data.

4. Medical visualisation device according to item 3, wherein the one or more components include the image sensor and the device processing unit is adapted to adjust settings of the image sensor, e.g. including colour, contrast, gain, and/or exposure settings, based on the settings data.

5. Medical visualisation device according to any of items 3-4, wherein the one or more components include the light emitter and the device processing unit is adapted to adjust settings of the light emitter, e.g. including current, brightness and/or PWM settings.

6. Medical visualisation device according to any of the preceding items, wherein the communication between the device wireless communication module and the monitor wireless communication module is in accordance with Wireless HD specification.

7. Medical visualisation device according to any of the preceding items, wherein the device wireless communication module is a wireless HD chipset.

8. Medical visualisation device according to any of the preceding items, wherein the image data has a first resolution, such as at least 400×400 pixels, and is generated at a first frame rate, such as at least 30 frames per second.

9. Medical visualisation device according to any of the preceding items, wherein the encoded image data uses a format with a total number of bits, such as 24 bits, and wherein a first portion of the total number of bits is used to encode the image data, wherein the first portion of the total number of bits is less than the total number of bits.

10. Medical visualisation device according to item 9, wherein the first portion of the first number of bits is 10 bits.

11. Medical visualisation device according to any of items 9-10 wherein a second portion of the total number of bits is used to embed additional information, such as battery status or settings information.

12. Medical visualisation device according to any of the preceding items, wherein the device wireless communication module is adapted to communicate with the monitor wireless communication module using a radio frequency at more than 10 GHz.

13. Medical visualisation device according to item 12, wherein the radio frequency is between 57-66 GHz, such as between 57-64 GHz, such as between 57.05-64 GHz, such as between 59-64 GHz, such as between 59.4-63.56, such as between 59.4-62.9 GHz.

14. Medical visualisation device according to any of the preceding items being an endoscope.

15. Medical visualisation device according to any of the preceding items, wherein the medical visualisation device comprises a handle and an insertion tube extending from the handle to a distal tube portion, and wherein the view from the visualisation device is a view from the distal tube portion of the insertion tube.

16. Medical visualisation device according to item 15, wherein the handle comprises a control button adapted to receive an input in a first input direction, and wherein the touch input in the first input direction causes a bendable section of the insertion tube to bend in a first bending direction.

17. Medical visualisation device according to any of items 1-13 being a laryngoscope.

18. Medical visualisation device according to any of the preceding items comprising a main device part comprising the image sensor and the light emitter, wherein the main device part is disposable, and the device processing unit and the device wireless communication module are provided in an auxiliary component adapted to be coupled to the main device part, wherein the auxiliary component is reusable.

19. Medical visualisation device according to item 18 as dependent on any of items 15 or 16, wherein the main device part comprises the handle and the insertion tube.

20. Medical visualisation device according to any of the preceding items, wherein the device wireless communication module comprises a device antenna.

21. Medical visualisation device according to any of the preceding items comprising a battery adapted to power the medical visualisation device.

22. Medical visualisation device according to item 21 as dependent on item 18, wherein the battery is provided in the auxiliary component.

23. Medical visualisation device according to any of items 21 or 22, wherein the battery is a rechargeable battery.

24. A monitor device operable to receive image data from a medical visualisation device, the monitor device comprising:

a first housing, a monitor wireless communication module adapted to communicate with a device wireless communication module of the medical visualisation device, the monitor wireless communication module being adapted to receive encoded image data using a downstream data channel from the device wireless communication module to the monitor wireless communication module, and wherein the monitor wireless communication module is adapted to transmit settings data using an upstream data channel from the monitor wireless communication module to the device wireless communication module, a monitor processing unit adapted to receive the encoded image data from the monitor wireless communication module and decode the encoded image data and cause a display to display a live representation of the image data.

25. Monitor device according to item 24 comprising the display, e.g. accommodated in the first housing.

26. Monitor device according to any of items 24-25, wherein the monitor processing unit is adapted to provide the settings data based on the image data to adjust settings of one or more components of the medical visualisation device.

27. Monitor device according to any of items 24-26, wherein the monitor wireless communication module comprises a monitor antenna, wherein the monitor antenna is positioned external to the first housing.

28. Monitor device according to item 27, wherein the monitor antenna is adapted to be positioned at a distance from the first housing of more than 2 meters.

29. Monitor device according to any of items 27 or 28, wherein the monitor antenna is adapted to be positioned above an operating setting in an operating room, such as at the ceiling of the operating room.

30. Monitor device according to any of items 27-29, wherein the monitor antenna is positioned above the first housing.

31. A medical visualisation system comprising a first medical visualisation device according to any of items 1-23 and a monitor device according to any of items 24-30.

32. Medical visualisation system according to item 31 comprising a second medical visualisation device according to any of items 1-23, wherein the first medical visualisation device and the second medical visualisation device are different.

33. Medical visualisation system according to item 32, wherein the first medical visualisation device is configured for a first clinical purpose and the second medical visualisation device is configured for a second clinical purpose.

34. Medical visualisation system according to any of items 32-33, wherein the image sensor of the first medical visualisation device is a first image sensor type and the image sensor of the second medical visualisation device is a second image sensor type.

35. Medical visualisation system according to any of items 31-34, at least as dependent on items 20 and 27, wherein the monitor antenna and the device antenna is positioned with line of sight there between.

The disclosure has been described with reference to a preferred embodiment. However, the scope of the invention is not limited to the illustrated embodiment, and alterations and modifications can be carried out without deviating from the scope of the invention.

Throughout the description, the use of the terms “first”, “second”, “third”, “fourth”, “primary”, “secondary”, “tertiary” etc. does not imply any particular order or importance but are included to identify individual elements. Furthermore, the labelling of a first element does not imply the presence of a second element and vice versa.

LIST OF REFERENCES

2 medical visualisation system
4 downstream data channel
6 upstream data channel
8 operator
10 patient
100, 100' medical visualisation device
110 main device part
112 image sensor
114 view
116 light emitter
118 handle
119 device button, e.g. image capture button
120 insertion tube
122 distal tube portion
124 control button
125A first input direction
125B second input direction
126 bendable section
128A first bending direction
128B second bending direction
130 main coupling part
132 main terminal
134 safety circuit
136 device identifier
140 main surface
142 main primary engagement member
146 primary surface
150 auxiliary component
152 auxiliary housing
154 device processing unit
155 auxiliary memory
156 device wireless communication module
158 device antenna
160 battery
170 auxiliary coupling part
172 auxiliary terminal
182 auxiliary primary engagement member
200 monitor device
202 first housing
204 display
206 monitor wireless communication module
207 monitor antenna
208 monitor processing unit
210 monitor memory
212 monitor button, e.g. image capture button
300 operating room
302 operating setting
304 ceiling

The invention claimed is:

1. A medical visualisation device comprising:

an image sensor configured to generate image data indicative of a view from the medical visualisation device, a light emitter configured to provide illumination of the view, a device processor configured to encode the image data with a battery status and/or settings information, to provide encoded image data having a format with a data transmission unit comprising a first subset of bits encoding the image data and a second subset of bits encoding the battery status and/or the settings information, and a device wireless transceiver configured to communicate with a monitor wireless transceiver of a monitor device concurrently with generation of the image data by the image sensor, the device wireless transceiver being configured to transmit the encoded image data to the monitor wireless transceiver using a downstream data channel from the device wireless transceiver.

2. The medical visualisation device of claim 1, wherein the device wireless transceiver is configured to receive settings data from the monitor wireless transceiver using an upstream data channel to the device wireless transceiver, wherein the settings data comprises one or more of colour, contrast, gain, and/or exposure, and wherein the device processor is configured to adjust a setting of the image sensor based on the settings data.

3. The medical visualisation device of claim 2, wherein the upstream data channel is limited to less than 500 bits per second.

4. The medical visualisation device of claim 1, wherein the device wireless transceiver is configured to receive settings data from the monitor wireless transceiver using an upstream data channel to the device wireless transceiver, and wherein the settings data comprises one or more of current, brightness and/or pulse width modulation (PWM) of the light emitter.

5. The medical visualisation device of claim 1, wherein the encoded image data uses a format with a total number of bits, wherein a first portion of the total number of bits is used for the image data, and wherein a second portion of the total number of bits is used to embed the battery status and/or the settings information.

6. The medical visualisation device of claim 1, wherein the device wireless transceiver is configured to communicate with the monitor wireless transceiver using a radio frequency at more than 10 GHz.

7. The medical visualisation device of claim 1, wherein the medical visualisation device comprises a handle and an insertion tube including a distal tube portion, the image sensor and the light emitter, the insertion tube extending from the handle, wherein the view from the visualisation device is a view from the distal tube portion of the insertion tube, wherein the handle comprises a control button configured to receive a touch input in a first input direction, and wherein the touch input in the first input direction causes a bendable section of the insertion tube to bend in a first bending direction.

8. The medical visualisation device of claim 1, wherein the medical visualization device comprises a main component comprising the image sensor and the light emitter, wherein the main component is configured for single-use, and the device processor and the device wireless transceiver are provided in an auxiliary component configured to be detachably coupled to the main component, wherein the auxiliary component is reusable and configured to be used with additional main components.

9. The medical visualisation device of claim 8, wherein the main component comprises a handle and an insertion tube including a distal tube portion, the image sensor and the light emitter, the insertion tube extending from the handle, wherein the handle comprises a control button configured to receive a touch input in a first input direction, and wherein the touch input in the first input direction causes a bendable section of the insertion tube to bend in a first bending direction.

10. A medical visualisation system comprising:

the medical visualisation device of claim 1; and the monitor device, the monitor device including:

a first housing, the monitor wireless transceiver, the monitor wireless transceiver being configured to communicate with the device wireless transceiver of the medical visualisation device, wherein the monitor wireless transceiver is configured to transmit settings data using an upstream data channel from the monitor wireless transceiver to the device wireless transceiver, a monitor processor configured to decode the encoded image data and cause a display to display a live representation of the image data, wherein the monitor processor is configured to provide the settings data based on the image data to adjust settings of one or more components of the medical visualisation device.

11. The medical visualisation system of claim 10, the monitor device further comprising the display accommodated in the first housing.

12. The medical visualisation system of claim 10, wherein the monitor wireless transceiver comprises a monitor antenna, and wherein the monitor antenna is positioned external to the first housing.

13. The medical visualisation system of claim 12, wherein the monitor antenna is configured to be positioned above an operating setting in an operating room.

14. The medical visualisation system of claim 10, the medical visualization system further comprising a second medical visualisation device according to claim 1, wherein the medical visualisation device and the second medical visualisation device are different.

15. The medical visualisation system of claim 14, wherein the medical visualisation device is configured for a first clinical purpose and the second medical visualisation device is configured for a second clinical purpose.

16. The medical visualisation system of claim 14, wherein the image sensor of the medical visualisation device is a first image sensor type and the image sensor of the second medical visualisation device is a second image sensor type.

17. The medical visualisation system of claim 10, further comprising:

a first main component including the image sensor and the light emitter;

a second main component including a second image sensor and a second light emitter;

an auxiliary component configured to be detachably coupled to the first main component and, not simultaneously, to the second main component, the auxiliary component comprising the device processor and the device wireless transceiver, wherein:

the image sensor is configured to generate first image data indicative of a view from the first main component, the light emitter is configured to provide illumination of the view from the first main component, the second image sensor is configured to generate second image data indicative of a view from the second main component, the second light emitter is configured to provide illumination of the view from the second main component, the device processor is configured to encode the first image data to provide first encoded image data based on the first image data and to encode the second image data to provide second encoded image data based on the second image data, the device wireless transceiver is configured to transmit the first encoded image data and the second encoded image data to the monitor wireless transceiver using the downstream data channel from the device wireless transceiver and to receive settings data from the monitor wireless transceiver using the upstream data channel to the device wireless transceiver, and the device processor is configured to adjust settings of one or more components of the first main component and the second main component based on the settings data.

18. The medical visualisation system of claim 17, wherein the first main component is different from the second main component.

* * * * *